(12) United States Patent
Tanioka et al.

(10) Patent No.: US 7,590,444 B2
(45) Date of Patent: Sep. 15, 2009

(54) IONTOPHORESIS DEVICE

(75) Inventors: Akihiko Tanioka, Ohota-ku (JP);
Akihiko Matsumura, Shibuya-ku (JP);
Takehiko Matsumura, Shibuya-ku (JP);
Mizuo Nakayama, Shibuya-ku (JP);
Hidero Akiyama, Shibuya-ku (JP)

(73) Assignee: TTI Ellebeau, Inc., Tokyo (JP)

( * ) Notice: Subject to any disclaimer, the term of this patent is extended or adjusted under 35 U.S.C. 154(b) by 509 days.

(21) Appl. No.: 11/172,372

(22) Filed: Jun. 30, 2005

(65) Prior Publication Data
US 2006/0129085 A1    Jun. 15, 2006

(30) Foreign Application Priority Data
Dec. 9, 2004   (JP)   ............................. 2004-357313

(51) Int. Cl.
*A61N 1/30*   (2006.01)
(52) U.S. Cl. ...................................................... 604/20
(58) Field of Classification Search ..................... 604/20
See application file for complete search history.

(56) References Cited

U.S. PATENT DOCUMENTS

| | | | |
|---|---|---|---|
| 3,891,786 A | 6/1975 | Conklin | 428/136 |
| 4,116,889 A | 9/1978 | Chlanda et al. | 521/27 |
| 4,140,121 A | 2/1979 | Kuhl et al. | 128/260 |
| 4,519,938 A | 5/1985 | Papir | 252/500 |
| 4,722,726 A | 2/1988 | Sanderson et al. | 604/20 |
| 4,731,049 A | 3/1988 | Parsi | 604/20 |
| 4,744,787 A | 5/1988 | Phipps et al. | 604/20 |
| 4,747,819 A | 5/1988 | Phipps et al. | 604/20 |
| 4,915,685 A | 4/1990 | Petelenz et al. | 604/20 |
| 4,927,408 A | 5/1990 | Haak et al. | 604/20 |
| 5,057,072 A | 10/1991 | Phipps | 604/20 |
| 5,080,646 A | 1/1992 | Theeuwes et al. | 604/20 |
| 5,084,006 A | 1/1992 | Lew et al. | 604/20 |
| 5,084,008 A | 1/1992 | Phipps | 604/20 |
| 5,135,477 A | 8/1992 | Untereker et al. | 604/20 |
| 5,147,296 A | 9/1992 | Theeuwes et al. | 604/20 |
| 5,162,043 A | 11/1992 | Lew et al. | 604/20 |
| 5,169,383 A | 12/1992 | Gyory et al. | 604/20 |
| 5,238,613 A | 8/1993 | Anderson | 264/22 |
| 5,322,502 A | 6/1994 | Theeuwes et al. | 604/20 |
| 5,326,341 A | 7/1994 | Lew et al. | 604/20 |
| 5,395,310 A | 3/1995 | Untereker et al. | 604/20 |
| 5,401,408 A | 3/1995 | Umemura et al. | 210/490 |

(Continued)

FOREIGN PATENT DOCUMENTS

CA    2205444    6/1996

(Continued)

OTHER PUBLICATIONS

U.S. Appl. No. 11/195,364, filed Aug. 2, 2005, Tanioka et al.

(Continued)

*Primary Examiner*—Nicholas D Lucchesi
*Assistant Examiner*—Victoria P Campbell
(74) *Attorney, Agent, or Firm*—Seed IP Law Group PLLC (57) ABSTRACT

An iontophoresis device for administering drug ions via the first ion-exchange membrane, comprising a first semi-permeable film having a number of pores passing through the film from a front surface to a back surface, a first ion-exchange membrane formed of ion-exchange resin filling the pores of the first semi-permeable film and selective ions of a first polarity, and a working electrode structure having a drug holding part placed on a back surface of the first ion-exchange membrane and holding a drug solution containing drug ions charged in the first polarity, wherein a layer of a water-soluble polymer compound is chemically bonded on the surface of the first semi-permeable film.

14 Claims, 3 Drawing Sheets

U.S. PATENT DOCUMENTS

| | | | |
|---|---|---|---|
| 5,405,317 A | 4/1995 | Myers et al. | 604/20 |
| 5,496,266 A | 3/1996 | Haak et al. | 604/20 |
| 5,503,632 A | 4/1996 | Haak | 604/20 |
| 5,543,098 A | 8/1996 | Myers et al. | 264/104 |
| 5,573,668 A | 11/1996 | Grosh et al. | 210/490 |
| 5,637,084 A | 6/1997 | Kontturi et al. | 604/20 |
| 5,647,844 A | 7/1997 | Haak et al. | 604/20 |
| 5,668,170 A | 9/1997 | Gyory | 514/449 |
| 5,711,761 A | 1/1998 | Untereker et al. | 604/20 |
| 5,788,666 A | 8/1998 | Atanasoska | 604/20 |
| 5,840,056 A | 11/1998 | Atanasoska | 604/20 |
| 5,840,339 A | 11/1998 | Kunin | 424/489 |
| 5,871,460 A | 2/1999 | Phipps et al. | 604/20 |
| 5,894,021 A | 4/1999 | Okabe et al. | 424/449 |
| 5,941,843 A | 8/1999 | Atanasoska et al. | 604/20 |
| 5,993,435 A | 11/1999 | Haak et al. | 604/501 |
| 6,049,733 A | 4/2000 | Phipps et al. | 604/20 |
| 6,064,908 A | 5/2000 | Muller et al. | 604/20 |
| 6,103,078 A | 8/2000 | Hitchems et al. | 204/296 |
| 6,109,852 A | 8/2000 | Shahinpoor et al. | 414/1 |
| 6,169,920 B1 | 1/2001 | Haak et al. | 604/20 |
| 6,256,533 B1 | 7/2001 | Yuzhakov et al. | 604/21 |
| 6,258,276 B1 | 7/2001 | Mika et al. | 210/638 |
| 6,314,317 B1 | 11/2001 | Willis | 604/20 |
| 6,329,488 B1 | 12/2001 | Terry et al. | 528/28 |
| 6,350,259 B1 | 2/2002 | Sage, Jr. et al. | 604/501 |
| 6,377,847 B1 | 4/2002 | Keusch et al. | 604/20 |
| 6,377,848 B1 | 4/2002 | Garde et al. | 604/20 |
| 6,385,488 B1 | 5/2002 | Flower et al. | 604/20 |
| 6,394,994 B1 | 5/2002 | Vilambi et al. | 604/501 |
| 6,402,732 B1 | 6/2002 | Flower et al. | 604/501 |
| 6,405,875 B1 | 6/2002 | Cutler | 210/477 |
| 6,454,941 B1 | 9/2002 | Cutler et al. | 210/266 |
| 6,462,935 B1 | 10/2002 | Shiue et al. | 361/511 |
| 6,468,657 B1 | 10/2002 | Hou et al. | 428/403 |
| 6,497,887 B1 | 12/2002 | Zecchino et al. | 424/401 |
| 6,503,957 B1 | 1/2003 | Bernatowicz | 521/27 |
| 6,522,919 B1 | 2/2003 | Flower et al. | 604/20 |
| 6,553,255 B1 | 4/2003 | Miller et al. | 604/20 |
| 6,584,349 B1 | 6/2003 | Sage, Jr. et al. | 604/20 |
| 6,629,968 B1 | 10/2003 | Jain et al. | 604/20 |
| 6,635,045 B2 | 10/2003 | Keusch et al. | 604/501 |
| 6,678,554 B1 | 1/2004 | Sun et al. | 604/20 |
| 6,678,555 B2 | 1/2004 | Flower et al. | 604/20 |
| 6,743,432 B1 | 6/2004 | Yanai et al. | 424/400 |
| 6,775,569 B2 | 8/2004 | Mori et al. | 604/20 |
| 6,858,018 B1 | 2/2005 | Green et al. | 604/19 |
| 6,862,473 B2 | 3/2005 | Keusch et al. | 604/20 |
| 6,918,901 B1 * | 7/2005 | Theeuwes et al. | 604/500 |
| 7,398,121 B2 | 7/2008 | Matsumura et al. | 604/20 |
| 2002/0022795 A1 | 2/2002 | Reynolds et al. | 604/20 |
| 2002/0058903 A1 * | 5/2002 | Murdock | 604/20 |
| 2002/0099320 A1 | 7/2002 | Beck | 604/20 |
| 2003/0065305 A1 | 4/2003 | Higuchi et al. | 604/501 |
| 2003/0088205 A1 | 5/2003 | Chandrasekaran et al. | 604/20 |
| 2003/0168404 A1 | 9/2003 | Mika et al. | 210/639 |
| 2004/0105881 A1 | 6/2004 | Cevc et al. | 424/450 |
| 2004/0138609 A1 | 7/2004 | Fukuta et al. | 604/20 |
| 2004/0167459 A1 | 8/2004 | Higuchi et al. | 604/20 |
| 2005/0011826 A1 | 1/2005 | Childs et al. | 210/490 |
| 2005/0070840 A1 | 3/2005 | Matsumura et al. | 604/20 |
| 2006/0083962 A1 | 4/2006 | Takekawa et al. | 429/13 |
| 2006/0095001 A1 | 5/2006 | Matsumura et al. | 604/20 |
| 2006/0116628 A1 | 6/2006 | Matsumura et al. | 604/20 |
| 2006/0129085 A1 | 6/2006 | Tanioka et al. | 604/20 |
| 2006/0135906 A1 | 6/2006 | Matsumura et al. | 604/20 |
| 2006/0173401 A1 | 8/2006 | Tanioka et al. | 604/20 |
| 2006/0198879 A1 | 9/2006 | Fukuta et al. | 424/448 |
| 2006/0211980 A1 | 9/2006 | Cormier et al. | 604/20 |
| 2006/0217654 A1 | 9/2006 | Matsumura et al. | 604/20 |
| 2006/0276742 A1 | 12/2006 | Matsumura et al. | 604/20 |
| 2007/0021711 A1 | 1/2007 | Matsumura et al. | 604/20 |
| 2007/0027426 A1 | 2/2007 | Matsumura et al. | 604/20 |
| 2007/0060859 A1 | 3/2007 | Kanamura et al. | 604/20 |
| 2007/0060860 A1 | 3/2007 | Nakayama et al. | 604/20 |
| 2007/0066930 A1 | 3/2007 | Tanioka et al. | 604/20 |
| 2007/0066931 A1 | 3/2007 | Kanamura et al. | 604/20 |
| 2007/0071807 A1 | 3/2007 | Akiyama et al. | 424/451 |
| 2007/0073212 A1 | 3/2007 | Matsumura | 604/20 |
| 2007/0078375 A1 | 4/2007 | Smith | 604/20 |
| 2007/0083147 A1 | 4/2007 | Smith | 604/20 |
| 2007/0088332 A1 | 4/2007 | Akiyama et al. | 604/890.1 |
| 2007/0093787 A1 | 4/2007 | Smith | 604/890.1 |
| 2007/0112294 A1 | 5/2007 | Akiyama et al. | 604/20 |
| 2007/0135754 A1 | 6/2007 | Akiyama et al. | 604/20 |
| 2007/0197955 A1 | 8/2007 | Akiyama et al. | 604/20 |
| 2007/0213652 A1 | 9/2007 | Carter | 604/20 |
| 2008/0213646 A1 | 9/2008 | Takekawa et al. | 429/33 |

FOREIGN PATENT DOCUMENTS

| | | |
|---|---|---|
| EP | 0 411 146 | 2/1991 |
| EP | 0 931 564 A1 | 7/1999 |
| EP | 1 440 707 | 7/2004 |
| EP | 1 566 197 | 8/2005 |
| GB | 2 265 088 | 9/1993 |
| JP | 52-151720 | 12/1977 |
| JP | 60-35936 | 2/1985 |
| JP | 03-094771 | 4/1991 |
| JP | 03-504343 | 9/1991 |
| JP | 04-297277 | 10/1992 |
| JP | 05/220385 | 8/1993 |
| JP | 8-164212 | 6/1996 |
| JP | 08-164212 | 6/1996 |
| JP | 09-201420 | 8/1997 |
| JP | 2792661 | 6/1998 |
| JP | 2-801083 | 7/1998 |
| JP | 10-510175 | 10/1998 |
| JP | 2845509 | 10/1998 |
| JP | 11-273452 | 10/1999 |
| JP | 30-40517 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-2373329 | 9/2000 |
| JP | 2000-288097 | 10/2000 |
| JP | 2000-288098 | 10/2000 |
| JP | 2001-505091 | 4/2001 |
| JP | 2001-120670 | 5/2001 |
| JP | 2002-233584 | 8/2002 |
| JP | 2004-188188 | 7/2004 |
| JP | 2004/188188 | 7/2004 |
| JP | 2004-202057 | 7/2004 |
| JP | 2004-292438 | 10/2004 |
| JP | 2004-317317 | 10/2004 |
| JP | 2004-357313 | 12/2004 |
| JP | 2005/503194 | 2/2005 |
| JP | 2006-149891 | 6/2006 |
| JP | 2006-212194 | 8/2006 |
| JP | 2007-037640 | 2/2007 |
| JP | 2007-050136 | 3/2007 |
| WO | 90/03825 | 4/1990 |
| WO | 90/04433 | 5/1990 |
| WO | 90/08571 | 8/1990 |
| WO | WO96/17648 | 6/1996 |
| WO | 97/47353 | 12/1997 |
| WO | WO02/100474 | 12/2002 |
| WO | 03/008078 | 1/2003 |

| | | |
|---|---|---|
| WO | WO03/037425 | 5/2003 |
| WO | 2004/073843 | 9/2004 |
| WO | 2006/062108 | 6/2006 |

OTHER PUBLICATIONS

U.S. Appl. No. 11/471,973, filed Jun. 20, 2006, Akihiko et al.
U.S. Appl. No. 11/475,838, filed Jun. 26, 2006, Matsumura et al.
U.S. Appl. No. 11/617,609, filed Dec. 28, 2006, Carter.
JIS (Japanese Industrial Standards), Testing Methods for Bubble Point of Membrane Filters, K3832, 11 pages, 1990.
Ito et al., "In Vitro Effect of Ion Exchange Membrane on Iontophoresis Medicine and Biology," 147(3); pp. 41-46, 2003.

* cited by examiner

Fig. 5

IONTOPHORESIS DEVICE

BACKGROUND OF THE INVENTION

1. Field of the Invention

The disclosure relates to an iontophoresis device for administering dissociated drug ions through an ion-exchange membrane that selects ions of the same polarity as that of the drug ions, capable of further enhancing the administration efficiency of the drug ions.

2. Description of the Related Art

An iontophoresis device generally includes a working electrode structure holding drug ions dissociated to positive or negative ions and a nonworking electrode structure that functions as a counterpart of the working electrode structure. The drug ions are administered to a living body by the application of a voltage with the same polarity as that of the drug ions to the working electrode structure under the condition that both the structures are in contact with a biological interface such as the skin or mucous membrane of the living body (e.g., human being or animal).

In this case, the charge supplied to the working electrode structure is consumed by the movement of the drug ions to the living body and the release of biological counter ions (the ions which are present in the living body and charged in a polarity type opposite to that of the drug ions), and the biological counter ions (e.g., $Na^+$ and $Cl^-$) having a small molecular weight and hence having a high mobility are released mainly from the living body. Thus, the ratio of the charge consumed by the release of biological counter ions increases, which makes it impossible to administer drug ions effectively.

JP 3040517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A, and WO 03/037425, the disclosures of which are incorporated herein by reference, disclose iontophoresis devices that have solved the above-mentioned problem.

More specifically, in each of the iontophoresis devices above, a working electrode structure is composed of an electrode, a drug holding part placed on a front side (in contact with the skin) of the electrode, and an ion-exchange membrane that is placed on a front side of the drug holding part and selectively passes ions with the same polarity as that of the drug ions held by the drug holding part, and the drug ions are administered through the ion-exchange membrane, whereby the release of biological counter ions is suppressed to enhance the administration efficiency of the drug.

In each of the iontophoresis devices above, the working electrode structure further includes an electrolyte solution holding part for holding an electrolyte solution in contact with the electrode, and an ion-exchange membrane that selectively passes ions having a polarity that is opposite to that of drug ions, thereby achieving the additional effects of preventing the drug ions from being decomposed by isolating the drug ions from the electrode and preventing the movement of $H^+$ or $OH^-$ ions generated at the electrode to the drug holding part and the biological interface of a living body.

Here, in the iontophoresis devices of JP 3040517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A, and WO 03/037425, in order to facilitate the passage of drug ions with a relatively large molecular weight and effectively suppressing the release of biological counter ions from a living body, an ion-exchange membrane is used in which a semi-permeable film made of polyolefin, vinyl chloride-based resin, fluorine-based resin, or the like is filled with ion-exchange resin (resin provided with an ion-exchange function). As such a semi-permeable film has low affinity for the biological interface of a living body, it is difficult to keep the contact between the ion-exchange membrane and the biological interface of the living body in a satisfactory state during the administration of drug ions, and depending upon the site which a working electrode structure and a nonworking electrode structure are brought into contact with, the behavior of the living body (patient) during the administration, and the like, the administration efficiency of drug ions cannot be maintained at a desired or sufficient level.

Therefore, the following inconvenience is caused. During the administration of the drug ions, it is necessary to interpose an electrolyte solution or the like between the ion-exchange membrane and the biological interface of the living body, or further keep pressing the working electrode structure and the nonworking electrode structure against the biological interface of the living body with some bias means.

The same kind of problem also arises in other devices that conduct the passage of a current to a living body, such as a low-frequency therapeutic equipment. In these devices, an adhesive film in which acrylic hydrogel is impregnated with an electrolyte solution is used, whereby the adhesion between the electrodes and the living body, and the conductivity are ensured.

However, when an adhesive film containing an electrolyte is interposed between the ion-exchange membrane and the skin, the function of the ion-exchange membrane in suppressing the release of biological counter ions from the biological interface degrades. Consequently, in the iontophoresis device for administering drug ions through an ion-exchange membrane, the administration efficiency of a drug cannot be enhanced by the use of this type of adhesive film.

BRIEF SUMMARY OF THE INVENTION

At least one embodiment may enhance the administration efficiency of a drug in an iontophoresis device for administering drug ions to a living body through an ion-exchange membrane.

In at least one embodiment, an iontophoresis device is capable of enhancing the administration efficiency of drug ions without the inconvenience of interposing an electrolyte solution between the ion-exchange membrane and the biological interface of a living body or the need to keep pressing a working electrode structure and/or a nonworking electrode structure to the living body with some bias means.

In at least one embodiment, an iontophoresis device for administering drug ions comprises a first a working electrode structure to which a first plurality of voltage source is applied, said working electrode structure having a first ion-exchange membrane including a first semi-permeable film with a number of pores communicating a front surface and a back surface of the first semi-permeable film and an ion-exchange resin being filled in the pores of the semi-permeable porous film, said first ion-exchange membrane selecting ions of a first polarity; and a drug holding part placed on a back surface side of the first ion-exchange membrane and holding a drug solution containing drug ions charged in the first polarity, and the above mentioned problem may be addressed by providing a first layer of a water-soluble polymer compound chemically bonded to a material constituting the first semi-permeable film on the front surface of the first semi-permeable film.

Although the mechanism for the remarkable enhancement of the administration efficiency of a drug according to the present teachings has not been necessarily clarified, it is considered that the following may contribute to the mechanism.

A water-soluble polymer compound chemically bonded to the front surface of the first semi-permeable film improves the affinity of an ion-exchange membrane with respect to the biological interface of a living body to some degree. Further, a layer of water bleeding or oozing out from the drug holding part is held at the first layer of the water-soluble polymer compound to enhance the conductivity between the ion-exchange resin and the biological interface. In addition, the first layer of the water-soluble polymer compound chemically bonded to the front surface of the semi-permeable film has a thickness from about one molecule to at most tens of molecules of the water-soluble polymer compound. Therefore, this layer does not substantially prevent the contact between the ion-exchange membrane and the biological interface, and in the same way as in the case where the layer of the water-soluble polymer compound is not present, the original function of the iontorophoresis device for administering drug ions through an ion-exchange membrane, i.e., the function of blocking the flow of biological counter ions from the biological interface while allowing the transfer of drug ions from the ion-exchange membrane to the biological interface is maintained.

The iontophoresis device may further include, as a counterpart structure of the above-mentioned working electrode structure (structure supplied with a voltage potential of a polarity opposite to that of the working electrode structure or grounded), a nonworking electrode structure that includes a second ion-exchange membrane including a second semi-permeable film with a number of pores communicating a front surface and a back surface of the second semi-permeable film and an ion-exchange resin being filled in the pores of the second semi-permeable film, said second ion-exchange membrane selecting ions of a second polarity opposite to the first polarity; and a first electrolyte solution holding part for holding an electrolyte solution, placed on a back surface side of the second ion-exchange membrane, and a second layer of a water-soluble polymer compound chemically bonded to a material constituting the second semi-permeable film may be formed on the front surface of the second semi-permeable film.

With this feature, the effect of enhancing the adhesion with respect to the biological interface and the conductivity in the nonworking electrode structure is achieved, and the administration efficiency of a drug is enhanced further.

The water-soluble polymer compound in the present invention is a polymer compound with molecular weight of about 50 to 1,000 which dissolves easily in water. Examples that may be particularly preferably used as the water-soluble polymer compound include polyvinyl alcohol (PVA), carboxymethylcellulose, polyacrylic acid, poly-N-isopropylacrylamide, polyacrylamide, poly-N-methylacrylamide, polyvinylpyrrolidone, polymethacrylic acid, polyethylene glycol, polyethyleneimine, poly-N-dimethylaminoethyl methacrylate, and polypeptide.

As the semi-permeable film, thermoplastic resin such as polyethylene resin or polypropylene resin may be preferred. The chemical bond (covalent bond) between the semi-permeable film and each of the above-mentioned water-soluble polymer compounds can be formed by irradiating the semi-permeable film immersed in an aqueous solution in which the water-soluble polymer compound is dissolved, with a UV-ray, an electron beam, a γ-ray, or plasma.

Each of the water-soluble polymer compounds as illustrated above has a straight-chain structure, and by appropriately controlling the reaction condition for chemically bonding the water-soluble polymer compound to the front surface of the semi-permeable film, the water-soluble polymer compound can be bonded to the front surface of the semi-permeable film in a brush shape. This can remarkably enhance the administration efficiency of a drug in particular. Similarly, by appropriately controlling the reaction condition, the water-soluble polymer compound can be bonded to the front surface of the semi-permeable film in a layer shape. Even in this case, the administration efficiency of a drug can be enhanced to a degree comparable to that in the case where the water-soluble polymer compound is bonded in a brush shape.

The water-soluble polymer compound can be chemically bonded to the front surface of the semi-permeable film before/after the semi-permeable film is filled with the ion-exchange resin or before/after the ion-exchange group is introduced into the ion-exchange resin. It may be preferable to chemically bond the water-soluble polymer compound to the front surface of the semi-permeable film after the semi-permeable film is filled with the ion-exchange resin, in order to prevent the adhesion of the water-soluble polymer compound to the walls of the pores of the semi-permeable film.

It is not necessarily required that the first and second layers of the water-soluble polymer compound are formed only on the front surface of the semi-permeable film and it is possible to form the first and second layers of the water-soluble polymer compound on both the front and back surfaces of the semi-permeable film.

Furthermore, in at least one embodiment, a third layer of a water-soluble polymer compound may be formed on the first or second layer of the water-soluble polymer compound chemically bonded to the front surface of the semi-permeable film.

The third layer absorbs water bled out from the drug holding part (or water supplied from outside if necessary) to be fluidized during the administration of drug ions. Therefore, when the working electrode structure and/or the nonworking electrode structure are brought into contact with the biological interface, the water-soluble polymer compound between the convex portion of the biological interface and the ion-exchange membrane moves to the space formed between the concave portion of the biological interface and the ion-exchange membrane, whereby the adhesion between the working electrode structure and/or the nonworking electrode structure, and the biological interface is further enhanced.

In order to obtain sufficient fluidity during the use, it may be preferable that the third layer is formed in such a way that the third layer does not chemically bond to the semi-permeable film, the ion-exchange resin, or the water-soluble polymer compound. For example, the third layer may be formed by coating, such as spin coating or bar coating, or immersing the semi-permeable film in an aqueous solution of the water-soluble polymer compound.

The water-soluble polymer compound constituting the third layer may include one or more of: polyvinyl alcohol (PVA), carboxymethylcellulose, polyacrylic acid, poly-N-isopropylacrylamide, polyacrylamide, poly-N-methylacrylamide, polyvinylpyrrolidone, polymethacrylic acid, polyethylene glycol, polyethyleneimine, poly-N-dimethylaminoethyl methacrylate, and polypeptide. A water-soluble polymer compound with molecular weight of about 1,000 to 1,000,000 which dissolves easily in water and can be used without any particular limit.

Thus, the adhesion and conductivity between a working electrode structure and/or a nonworking electrode structure, and the biological interface of a living body may be advantageously enhanced, while the release of biological counter ions from the biological interface is minimized, whereby the administration efficiency of drug ions with respect to a living body can be enhanced.

Furthermore, as a result of the achievement of the above-mentioned functional effect, an iontophoresis device capable of administering drug ions stably to a living body with a high administration efficiency can be realized, without interposing an electrolyte solution between the working electrode structure and/or the nonworking electrode structure, and the biological interface of a living body, or without using bias means for maintaining a pressing of the working electrode structure and/or the nonworking electrode structure against the living body, depending upon a site of the living body which the working electrode structure and/or the nonworking electrode structure is brought into contact with.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DESCRIPTION OF THE PREFERRED EMBODIMENTS

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with iontophoresis, controller, voltage or current sources, and/or membranes have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
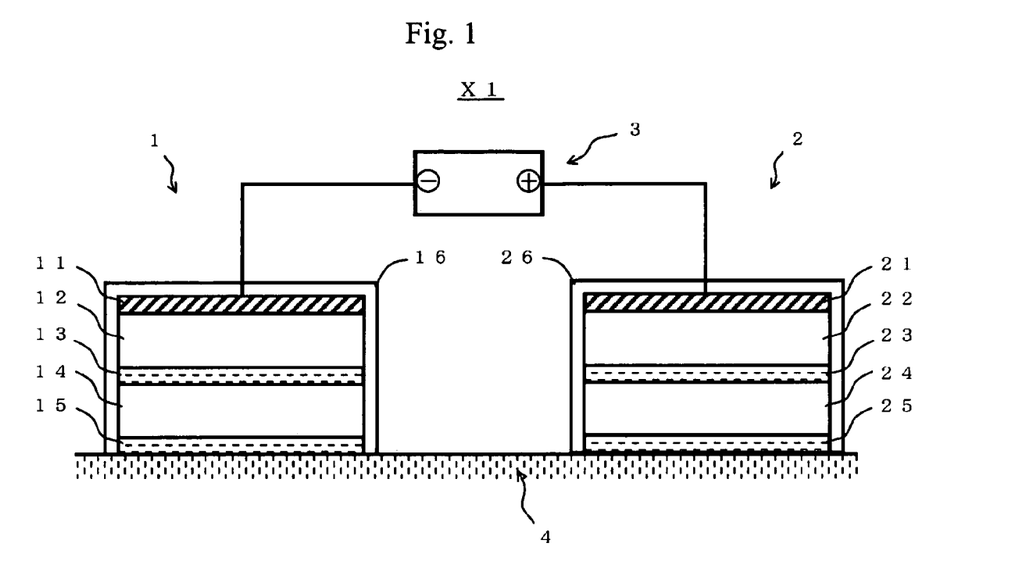
FIG. 1 is a cross-sectional view showing a basic configuration of an iontophoresis device in use on a biological interface according to one illustrated embodiment.

FIG. 1 is a schematic cross-sectional view showing a basic configuration of an iontophoresis device X1.

In the following, for convenience of description, an iontophoresis device for administering a drug whose drug component is dissociated to negative ions (for example, ascorbic acid that is a vitamin agent, lipid A used as an adjuvant for vaccine) will be exemplified. In the case of an iontophoresis device for administering a drug whose drug component is dissociated to positive ions (for example, lidocaine that is an anesthetic agent, calnitine chloride that is a gastrointestinal disease therapeutic agent, pancuronium bromide that is a skeletal muscle relaxant, morphine hydrochloride that is an anesthetic agent), the polarity (positive or negative) of a power source, each electrode, and each ion-exchange membrane in the following description is reversed.

As shown, an iontophoresis device X1 includes a working electrode structure 1, a nonworking electrode structure 2, and a power source 3, as main components (members). Reference numeral 4 denotes a biological interface such as skin or a mucous membrane.

The working electrode structure 1 includes an electrode 11 connected to a negative pole of the power source 3, an electrolyte solution holding part 12 for holding an electrolyte solution in contact with the electrode 11, a cation exchange membrane 13 placed on a front surface side of the electrolyte solution holding part 12, a drug holding part 14 placed on a front surface side of the cation exchange membrane 13, and an anion exchange membrane 15 placed on a front surface side of the drug holding part 14. The entire working electrode structure 1 may be housed in a cover or a container 16 composed of a material such as a resin film or a plastic.

On the other hand, the nonworking electrode structure 2 includes an electrode 21 connected to a positive pole of the power source 3, an electrolyte solution holding part 22 for holding an electrolyte solution in contact with the electrode 21, an anion exchange membrane 23 placed on a front surface side of the electrolyte solution holding part 22, an electrolyte solution holding part 24 placed on a front surface side of the anion exchange membrane 23, and a cation exchange membrane 25 placed on a front surface side of the electrolyte solution holding part 24. The entire nonworking electrode structure 2 may be housed in a cover or a container 26 composed of a material such as a resin film or a plastic.

In the iontophoresis device X1, those which are made of any conductive material can be used as the electrodes 11 and 21 without any particular limit. In particular, a inactive electrode composed of carbon, platinum, or the like may be preferable, and a carbon electrode without any possibility of the elution of metal ions and the transfer thereof to a living body can be even more preferable.

However, an active electrode such as a silver/silver chloride couple electrode in which the electrode 11 is made of silver chloride and the electrode 21 is made of silver can also be adopted.

For example, in the case of using the silver/silver chloride couple electrode, in the electrode 21 that is an anode (positive) pole, a silver electrode and chlorine ions (Cl$^-$) easily react with each other to generate insoluble AgCl as represented by Ag$^+$Cl$^-$→AgCl+e$^-$, and in the electrode 11 that is a cathode (negative pole), chlorine ions (Cl$^-$) are eluted from a silver chloride electrode. Consequently, the electrolysis of water may advantageously be suppressed, and the rapid acidification based on H$^+$ ions at the anode, and the rapid basification based on OH$^-$ ions at the cathode may advantageously be prevented.

In contrast, in the working electrode structure 1 and the nonworking electrode structure 2 in the iontophoresis device X1 in FIG. 1, owing to the function of the anion exchange membrane and/or the cation exchange membrane, the rapid basification based on OH$^-$ ions in the electrolyte solution holding part 12 and the rapid acidification based on H$^+$ ions in the electrolyte solution holding part 22 are suppressed. Therefore, an inexpensive carbon electrode without any possibility of the elution of metal ions can be used preferably in place of the active electrode such as a silver/silver chloride couple electrode.

The electrolyte solution holding parts 12, 22, and 24 in the iontophoresis device X1 in FIG. 1 hold an electrolyte solution for keeping the conductivity. Phosphate buffered saline, physiological saline, etc. can be used as the electrolyte solution typically.

Furthermore, in order to more effectively prevent the generation of gas caused by the electrolytic reaction of water and the increase in a conductive resistance caused by the generation of gas, or the change in pH caused by the electrolytic reaction of water, a compound that is more easily oxidized or reduced than the electrolytic reaction (oxidation at the positive pole and the reduction at the negative pole) of water can be added to the electrolyte solution holding parts 12 and 22. In terms of the biological compatibility, safety and economic efficiency (low cost and easy availability), for example, an inorganic compound such as ferrous sulfate or ferric sulfate, a medical agent such as ascorbic acid (vitamin C) or sodium ascorbate, an acidic compound that is present on the surface of a biological interface such as lactic acid, and an organic acid such as oxalic acid, malic acid, succinic acid, or fumaric acid and/or a salt thereof can be used preferably. Alternatively, a combination of those substances (for example, 1:1 mixed aqueous solution containing 1 mol (M) of lactic acid and 1 mol (M) of sodium fumarate) can also be used.

Regarding the electrolyte solution holding part 12, in order to avoid the change in composition owing to the mixture with a drug solution held in a drug holding part 14 (described later), the drug solution having the same composition as that of the drug solution held in the drug holding part 14 can also be used.

Regarding the electrolyte solution holding parts 22 and 24, in order to avoid the change in composition owing to the mixture of an electrolyte solution in the electrolyte solution holding parts 22 and 24, the electrolyte solution with the same composition can be used.

The electrolyte solution holding parts 12, 22, and 24 may hold the above-mentioned electrolyte solution in a liquid state. However, the electrolyte solution holding parts 12, 22, and 24 may be configured by impregnating a water-absorbing thin film carrier made of a polymer material or the like with the above-mentioned electrolyte solution, thereby enhancing the ease of handling thereof. The same thin film carrier as that can be used in the drug holding part 14 can also be used as the thin film carrier used herein. Therefore, the detail thereof will be described in the following description regarding the drug holding part 14.

The drug holding part 14 in the iontophoresis device X1 according to this embodiment holds at least an aqueous solution of a drug (for example, ascorbic acid) whose active ingredient is dissociated to negative ions by the dissolution, as a drug solution.

Here, the drug holding part 14 may hold a drug solution in a liquid state. However, it is also possible to impregnate such a water-absorbing thin film carrier as described below with a drug solution so as to enhance the ease of handling thereof.

Examples of a material that can be used for the water-absorbing thin film carrier in this case include a hydrogel body of acrylic-based resin (acrylhydrogel film), segmented polyurethane-based gel film, and an ion conductive semipermeable or porous sheet for forming a gel solid electrolyte. By impregnating the above aqueous solution at an impregnation ratio of 20 to 60%, a high transport number (high drug delivery property), e.g., 70 to 80% can be obtained.

The impregnation ratio in the present specification is represented by % by weight (i.e., $100 \times (W-D)/D[\%]$ where D is a weight in a dry state and W is a weight after impregnation). The impregnation ratio should be measured immediately after the impregnation with an aqueous solution to eliminate an influence with time.

Furthermore, the transport number in the present specification refers to the ratio of a current that contributes to the transfer of drug ions among all the currents flowing through the working electrode structure. The transport number should be measured in such a manner that another constituent member is assembled with a thin film impregnated with a drug solution interposed between the ion-exchange membranes 13 and 15 so as to minimize the change with time.

Herein, the above-mentioned acrylhydrogel film (for example, available from Sun Contact Lens Co., Ltd.) is a gel body having a three-dimensional network structure (cross-linking structure). When an electrolyte solution that is a dispersion medium is added to the acrylhydrogel film, the acrylhydrogel film becomes a polymer adsorbent having ion conductivity. Furthermore, the relationship between the impregnation ratio of the acrylhydrogel film and the transport number can be adjusted depending upon the size of the three-dimensional network structure and the kind and ratio of a monomer constituting a resin. The acrylhydrogel film with an impregnation ratio of 30 to 40% and a transport number of 70 to 80% can be prepared from 2-hydroxyethylmethacrylate and ethyleneglycol dimethacrylate (monomer ratio 98 to 99.5:0.5 to 2), and it is confirmed that the impregnation ratio and transport number are almost the same in a range of an ordinary thickness of 0.1 to 1 mm.

Furthermore, the segmented polyurethane gel film has, as segments, polyethylene glycol (PEG) and polypropylene glycol (PPG), and can be adjusted based on a monomer and diisocyanate constituting these segments. The segmented polyurethane gel film has a three-dimensional structure cross-linked by a urethane bond, and the impregnation ratio, transport number, and adhesion strength of the gel film can be easily adjusted by controlling the size of a network, and the kind and ratio of a monomer in the same way as in the acrylhydrogel film. When water that is a dispersion medium and an electrolyte (alkaline metal salt, etc.) are added to the segmented polyurethane gel film (porous gel film), oxygen in an ether connecting part of polyether forming a segment and an alkaline metal salt form a complex, and ions of the metal salt move to oxygen in a subsequent blank ether connecting part when a current flows, whereby the conductivity is expressed.

As the ion conductive semi-permeable sheet for forming a gel solid electrolyte, for example, there is the one disclosed in JP 11-273452 A. This semi-permeable sheet is based on an acrylonitrile copolymer, and a semi-permeable polymer with a porosity of 20 to 80%. More specifically, this semi-permeable sheet is based on an acrylonitrile-based copolymer with a porosity of 20 to 80% containing 50 mol % or more (preferably 70 to 98 mol %) of acrylonitrile. The acrylonitrile-based gel solid electrolytic sheet (solid-state battery) is prepared by impregnating an acrylonitrile-based copolymer sheet soluble in a non-aqueous solvent and having a porosity of 20 to 80%, with a non-aqueous solvent containing an electrolyte, followed by gelling, and a gel body includes a gel to a hard film.

In terms of the ion conductivity, safety, and the like, the acrylonitrile-based copolymer sheet soluble in a non-aqueous solvent may be composed of an acrylonitrile/C1 to C4 alkyl (meth)acrylate copolymer, an acrylonitrile/vinylacetate copolymer, an acrylonitrile/styrene copolymer, an acrylonitrile/vinylidene chloride copolymer, or the like. The copolymer sheet is made semi-permeable or porous by an ordinary method such as a wet (dry) paper making method, a needlepunching method that is a kind of a non-woven fabric producing method, a water-jet method, drawing perforation of a melt-extruded sheet, or perforation by solvent extraction. In the present invention, among the above-mentioned ion conductive semi-permeable sheets of an acrylonitrile-based copolymer used in a solid-state battery, a gel body (a gel to a hard film) holding the above-mentioned aqueous solution in a three-dimensional network of a polymer chain and in which the above-mentioned impregnation ratio and transport number are achieved is useful as a thin film carrier used in the drug holding part 14 or the electrolyte solution holding parts 12, 22, and 24.

Regarding the conditions for impregnating the above-mentioned thin film carrier with a drug solution or an electrolyte solution, the optimum conditions may be determined in terms of the impregnation amount, impregnation speed, and the like. For example, an impregnation condition of 30 minutes at 40° C. may be selected.

In the iontophoresis device X1, an ion-exchange membrane in which a part or an entirety of the pores of the semi-permeable film is filled with ion-exchange resin having a cation exchange function can be used as the cation exchange membranes 13 and 25, and an ion-exchange membrane filled with ion-exchange resin having an anion exchange function can be used as the anion exchange membranes 15 and 23. For example, the NEOSEPTA cation-exchange membranes CM-1, CM-2, CMX, CMS, CMB, CLE04-2, etc. produced by Tokuyama Co., Ltd. can be used as the cation exchange membranes 13 and 15. The NEOSEPTA anion-exchange membranes AM-1, AM-3, AMX, AHA, ACH, ACS, ALE04-2, AIP-21, etc. produced by Tokuyama Co., Ltd. can be used as the anion ion-exchange membranes 15 and 23.

Herein, a fluorine type resin with an ion-exchange group introduced to a perfluorocarbon skeleton or a hydrocarbon type resin containing a resin that is not fluorinated as a skeleton can be used as the above-mentioned ion-exchange resin. In view of the convenience of a production process, a hydrocarbon type ion-exchange resin may be preferred. Furthermore, although the filling ratio of the ion-exchange resin is also related to the porosity of the semi-permeable or porous film, the filling ratio is generally 5 to 95% by mass, in particular, 10 to 90% by mass, and preferably 20 to 60% by mass.

There is no particular limit to an ion-exchange group of the above-mentioned ion-exchange resin, as long as it is a functional group generating a group having negative or positive charge in an aqueous solution. As specific examples of the functional group to be such an ion-exchange group, those of a cation exchange group include a sulfonic acid group, a carboxylic acid group, and a phosphonic acid group. Those acid groups may be present in the form of a free acid or a salt. Examples of a counter cation in the case of a salt include alkaline metal cations such as sodium ions and potassium ions, and ammonium ions. In those cation exchange groups, generally, a sulfonic acid group that is a strong acidic group may be particularly preferred. Examples of the anion exchange group include primary to tertiary amino groups, a quaternary ammonium group, a pyridyl group, an imidazole group, a quaternary pyridinium group, and a quaternary imidazolium group. Examples of a counter anion in those anion exchange groups include halogen ions such as chlorine ions and hydroxy ions. In those anion exchange groups, generally, a quaternary ammonium group and a quaternary pyridinium group that are strong basic groups are used.

As the above-mentioned semi-permeable film, it is possible to use a film or a sheet having a number of pores communicating a front side and a back side thereof, such as a single film formed by extrusion, calendaring, or the like in which the pores in the form of continuous air holes capable of carrying the ion-exchange resin are formed, and a film formed of woven fabric or non-woven fabric of a fibrous material in which the ion-exchange resin is carried in the pores formed by a gap between fibers, without any particular limit. In order to satisfy both high strength and flexibility, the semi-permeable film may be made of thermoplastic resin.

Examples of the thermoplastic resins constituting the semi-permeable film include, without limitation: polyolefin resins such as homopolymers or copolymers of α-olefins such as ethylene, propylene, 1-butene, 1-pentene, 1-hexene, 3-methyl-1-butene, 4-methyl-1-pentene, and 5-methyl-1-heptene; vinyl chloride resins such as polyvinyl chloride, vinyl chloride-vinyl acetate copolymers, vinyl chloride-vinylidene chloride copolymers, and vinyl chloride-olefin copolymers; fluorine resins such as polytetrafluoroethylene, polychlorotrifluoroethylene, polyvinylidene fluoride, tetrafluoroethylene-hexafluoropropylene copolymers, tetrafluoroethylene-perfluoroalkyl vinylether copolymers, and tetrafluoroethylene-ethylene copolymers; polyamide resins such as nylon 6 and nylon 66; and those which are made from polyamide resins. Polyolefin resins may be used as they are superior in mechanical strength, flexibility, chemical stability, and chemical resistance, and have good compatibility with ion-exchange resins. As the polyolefin resins, polyethylene and polypropylene may be particularly preferred and polyethylene may be most preferred.

There is no particular limit to the property of the above-mentioned semi-permeable film made of the thermoplastic resin. However, the average pore diameter of the pores may preferably be approximately 0.005 to 5.0 μm, more preferably approximately 0.01 to 2.0 μm, and may most preferably be approximately 0.02 to 0.2 μm since the semi-permeable film having such an average pore diameter is likely to be a thin ion-exchange membrane having excellent strength and a low electric resistance. The average pore diameter in the present specification refers to an average flow pore diameter measured in accordance with a bubble point method (JIS K3832-1990). Similarly, the porosity of the semi-permeable film may be preferably 20 to 95%, more preferably 30 to 90%, and most preferably 30 to 60%. Furthermore, the thickness of the semi-permeable film may be preferably approximately 5 to 140 μm, or may more preferably be approximately 10 to 120 µm, and may most preferably be approximately 15 to 55 µm. Usually, an anion exchange membrane or a cation exchange membrane using such a semi-permeable film has a thickness approximately +0 to 20 µm.

Regarding the semi-permeable film used for the anion exchange membrane 15 and the cation exchange membrane 25, before or after the filling of the ion-exchange resin or the introduction of the ion-exchange group, a water-soluble polymer compound is chemically bonded to the front surface (the surface opposing to the biological interface 4), whereby first and second layers of the water-soluble polymer compound are formed.

Examples of the water-soluble polymer compound include polymer compounds having a molecular weight of about 50 to 1,000 dissolved easily in water, such as polyvinyl alcohol (PVA), carboxymethylcellulose, polyacrylic acid, poly-N-isopropylacrylamide, polyacrylamide, poly-N-methylacrylamide, polyvinylpyrrolidone, polymethacrylic acid, polyethylene glycol, polyethyleneimine, poly-N-dimethylaminoethyl methacrylate, and polypeptide. A water-soluble polymer compound can be chemically bonded to the front surface of the semi-permeable film by irradiating the semi-permeable film immersed in an aqueous solution in which the water-soluble polymer compound is dissolved, with a UV-ray, an electron beam, a γ-ray, or plasma.

Each of the above-mentioned water-soluble polymer compounds has a straight-chain structure, and by appropriately controlling the reaction condition in the above-mentioned treatment, such as concentration or temperature of the water-soluble polymer compound or the irradiation amount of a UV-ray, an electron beam, a γ-ray, or plasma, the water-soluble polymer compound can be bonded to the front surface of the semi-permeable film in a brush shape. Depending upon the reaction condition, the first and second layers can be formed in such a way that a single molecule of the water-soluble polymer compound is bonded to the front surface of the semi-permeable film in a brush shape, or in such a way that a plurality of (several to tens of) water-soluble polymer compounds connected in a chain-length direction are bonded to the front surface of the semi-permeable film in a brush shape.

As the anion exchange membrane 15 and the cation exchange membrane 25, a semi-permeable film can also be used in which a third layer made of a water-soluble polymer compound is laminated on the first and second layers of the water-soluble polymer compound formed as described above.

As the water-soluble polymer compound used for the third layer, it is possible to use polymer compounds having a molecular weight of, for example, about 1,000 to 1,000,000 dissolved easily in water, such as polyvinyl alcohol (PVA), carboxymethylcellulose, polyacrylic acid, poly-N-isopropylacrylamide, polyacrylamide, poly-N-methylacrylamide, polyvinylpyrrolidone, polymethacrylic acid, polyethylene glycol, polyethyleneimine, poly-N-dimethylaminoethyl methacrylate, and polypeptide. The third layer can be formed by coating and drying an aqueous solution of these water-soluble polymer compounds diluted to an appropriate concentration by a method such as spin coating or bar coating.

The thickness of the third layer made of a water-soluble polymer compound may be in a range of 1 to 200 µm.

Figure 2:
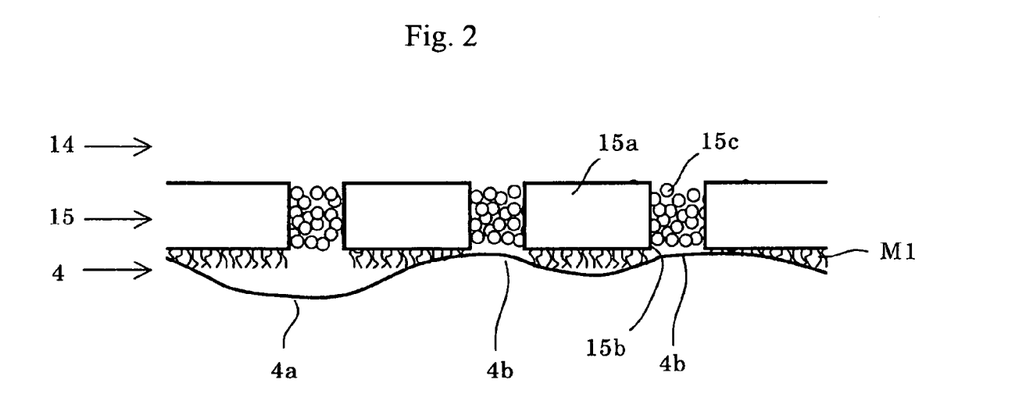
FIG. 2 is a partial cross-sectional view schematically showing a situation in which an ion-exchange membrane used in the iontophoresis device is in contact with the biological interface.

FIG. 2 is a conceptual explanatory view showing a state where an ion-exchange membrane 15 using a semi-permeable film 15a with a first layer M1 of a water-soluble polymer compound bonded to the front surface thereof in a brush shape is in contact with a biological interface 4 having concave portions 4a and convex portions 4b.

As shown, in the case of using the ion-exchange membrane 15 for the working electrode structure 1, owing to the presence of the first layer M1 of the water-soluble polymer compound bonded to the front surface of the semi-permeable film 15a in a brush shape, the contact area with respect to the skin 4 increases. Furthermore, the water of a drug holding part 14 bleeding out from openings 15b of the semi-permeable film 15a is held in the first layer M1, whereby the adhesion and conductivity between the skin 4 and the ion-exchange membrane 15 are expected to be enhanced.

Simultaneously, portions such as the convex portions 4b of the biological interface close to the openings 15b of the semi-permeable film 15a hold the original function of an iontophoresis device for administering drug ions via an ion-exchange membrane, i.e., the function of suppressing the release of biological counter ions from the biological interface 4 by the ion-exchange resin 15c being filled in the pores of the semi-permeable film 15a, while allowing drug ions to move from the ion-exchange resin 15c to the biological interface 4.

In the concave portions 4a of the biological interface 4, a layer of the water bleeding out from the openings 15b is formed, and consequently, the adhesion and the conductivity between the biological interface 4 and the ion-exchange membrane 15 are expected to be enhanced. On the other hand, a part of charge supplied to the working electrode structure is considered to be consumed by the release of biological counter ions from the biological interface 4 to the layer of the water. However, the volume of such water layer is very small, so that the charge amount consumed by this release is considered to be negligible.

Figure 3A:
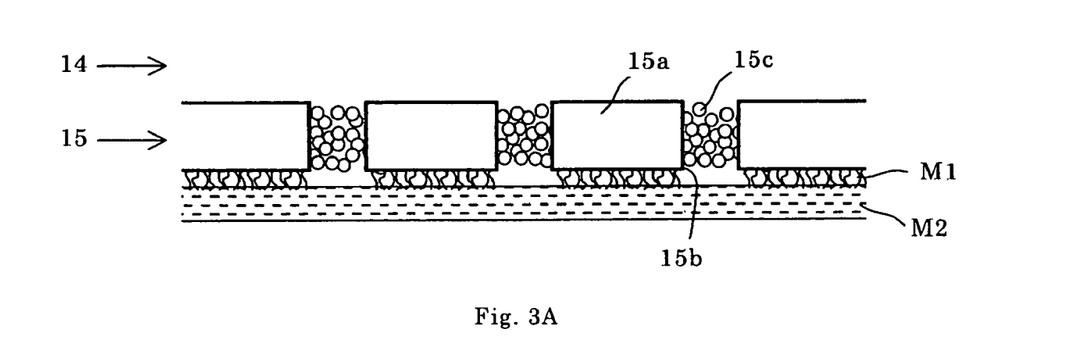
FIG. 3A is a partial cross-sectional view schematically showing an ion-exchange membrane used in the iontophoresis device.
Figure 3B:
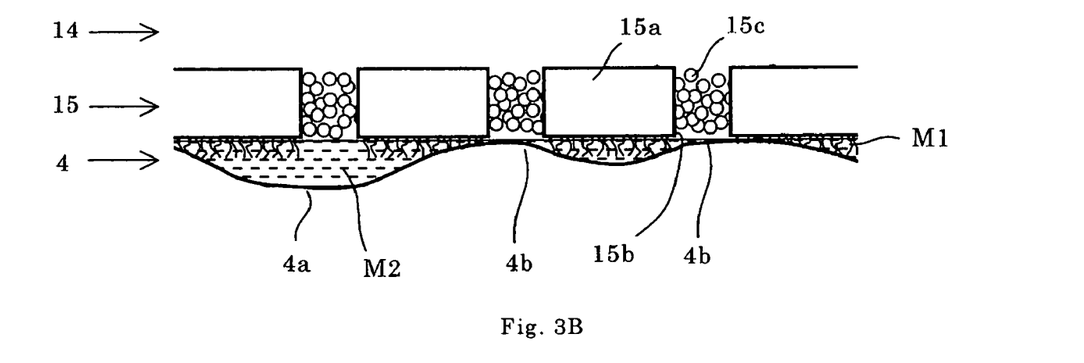
FIG. 3B is a partial cross-sectional view schematically showing a situation in which the ion-exchange membrane is in contact with the biological interface.

FIG. 3A is a conceptual explanatory view showing an ion-exchange membrane 15 using a semi-permeable film 15a with a third layer M2 made of a water-soluble polymer compound further formed on a first layer M1 of the water-soluble polymer compound similar to that of FIG. 2. FIG. 3B is a conceptual explanatory view showing a state where the ion-exchange membrane 15 is in contact with the biological interface 4 having concave portions 4a and convex portions 4b.

As shown in FIG. 3A, the third layer M2 is formed to some thickness on the first layer M1. The third layer M2 is capable of flowing easily owing to the water bleeding out from the openings 15b. When the ion-exchange membrane 15 is brought into contact with the biological interface 4, as shown in FIG. 3B, the water-soluble polymer compound between the convex portions 4b of the biological interface and the ion-exchange membrane 15 moves to the space between the concave portions 4a and the ion-exchange membrane 15.

Therefore, the adhesion and the conductivity between the ion-exchange membrane 15 and the biological interface 4 become more satisfactory. On the other hand, the third layer M2 is not present between the convex portions 4b of the biological interface and the ion-exchange membrane 15, or is present as a very thin film. Therefore, the convex portions 4b of the biological interface close to the openings 15b of the semi-permeable film 15a hold the original function of an iontophoresis device for administering drug ions via an ion-exchange membrane, i.e., the function of suppressing the release of biological counter ions from the biological interface 4 by the ion-exchange resin 15c, while allowing drug ions to move from the ion-exchange resin 15c to the biological interface 4.

For the ion-exchange membrane 25 of the nonworking electrode structure 2, it is also possible to use a semi-permeable film having a second layer of a water-soluble polymer compound bonded to the front surface in a brush shape in the same way as the above, or a third layer of a water-soluble polymer compound further laminated on the second layer in the same way as the above, whereby the adhesion and conductivity between the ion-exchange membrane 25 and the biological interface 4 can be enhanced.

As the power source 3 in the iontophoresis device of the present invention, a battery, a voltage stabilizer, a current stabilizer (galvano device), a voltage/current stabilizer, or the like can be used. It may be preferable to use a current stabilizer that is operated under safe voltage conditions in which an arbitrary current can be adjusted in a range of 0.01 to 1.0 mA, or may be preferable in a range of 0.01 to 0.5 mA, specifically, at 50V or less, or may be preferably, 30 V or less.

Figure 4:
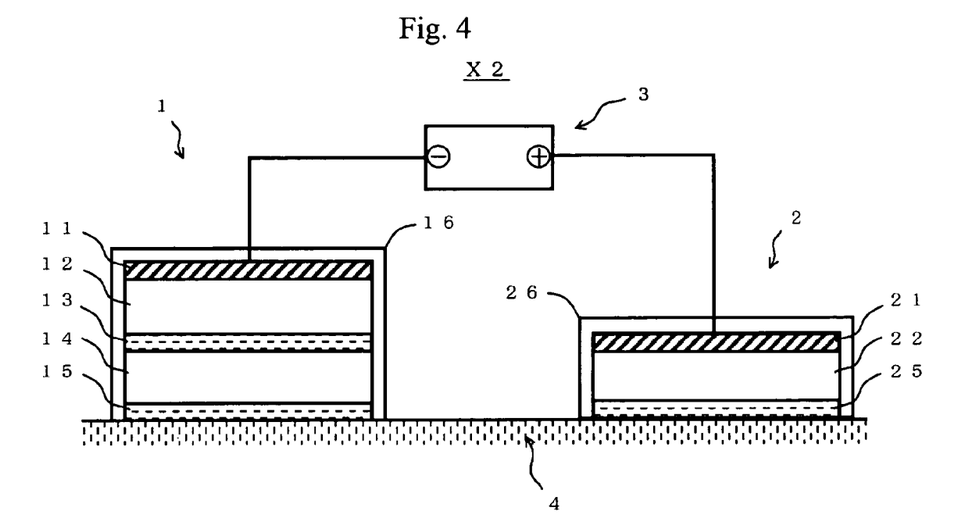
FIG. 4 is a cross-sectional view showing a configuration of an iontophoresis device in use on a biological interface according to another illustrated embodiment.
Figure 5:
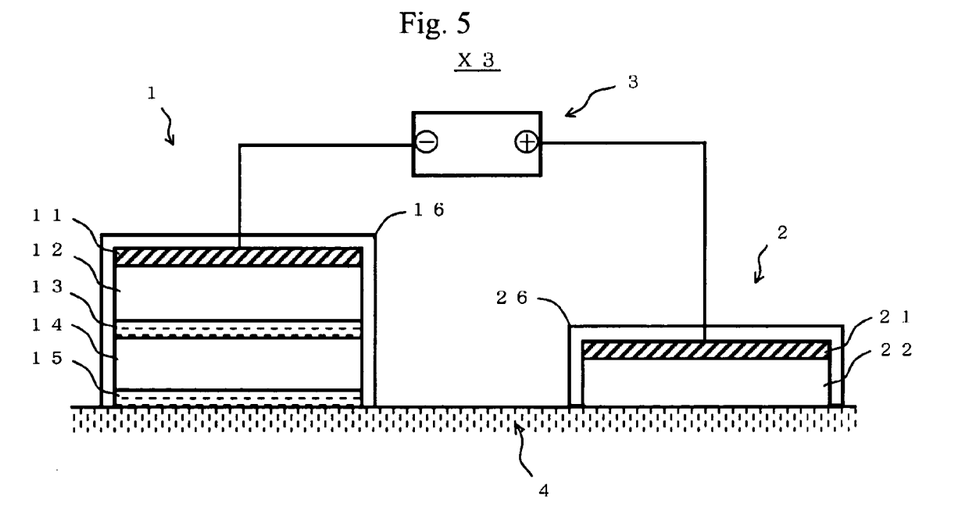
FIG. 5 is a cross-sectional view showing a configuration of an iontophoresis device in use on a biological interface according to another illustrated embodiment.

FIGS. 4 and 5 are explanatory views showing configurations of iontophoresis devices X2 and X3 according to other embodiments.

The iontophoresis device X2 in FIG. 4 has the same configuration as that of the iontophoresis device X1 shown in FIG. 1 except that the nonworking electrode structure 2 does not have the ion-exchange membrane 23 and the electrolyte solution holding part 24. The iontophoresis device X3 in FIG. 5 has the same configuration as that of the iontophoresis device X1 shown in FIG. 1 except that the nonworking electrode structure 2 does not have the ion-exchange membranes 23 and 25, and the electrolyte solution holding part 24. Although the iontophoresis devices X2 and X3 are not comparable to the iontophoresis device X1 in terms of the performance of suppressing the change in pH on the contact surface of the nonworking electrode structure 2 with respect to the biological interface 4, they exhibit performance similar to that of the iontophoresis device X1 in the other points. In particular, owing to the anion exchange membrane 15 and/or the cation exchange membrane 25 having the first and second layers M1 of a water-soluble polymer compound or further the third layer M2 on the surface front thereof, the iontophoresis devices X2 and X3 exhibit the functional effect of stably administering drug ions at a high efficiency, compared with the conventional iontophoresis devices.

The present invention has been described with reference to the illustrated embodiments. The present invention is not limited thereto, and various alterations can be made within the scope of the claims.

For example, in the above embodiment, the case has been described in which the first layer is formed on the ion-exchange membrane 15 of the working electrode structure 1, and the second layer is formed on the ion-exchange membrane 25 of the nonworking electrode structure 2. An iontophoresis device in which the first layer is formed on the ion-exchange membrane 15 of the working electrode structure 1, while the second layer is not formed on the ion-exchange membrane 25 of the nonworking electrode structure 2 is also included in the scope of the present invention.

Although, in the above embodiment, the case has been described in which the working electrode structure 1 has the electrolyte solution holding part 12 and the ion-exchange membrane 13 in addition to the electrode 11, the drug holding part 14, and the ion-exchange membrane 15, the electrolyte holding part 12 and the ion-exchange membrane 13 can be omitted. In this case, the function of suppressing the decomposition of a drug in the vicinity of the electrode 11, the function of suppressing the movement of $H^+$ ions and $OH^-$ ions to the biological interface or the change in pH at the biological interface caused by the movement of ions, and the like are not comparable to those in the above-mentioned embodiment. However, the enhancement of the administration efficiency of drug ions to a living body is similarly achieved. Such an iontophoresis device is also included in the scope of the present invention.

Similarly, in the nonworking electrode structure 2, the following may be possible. The electrolyte solution holding parts 22 and 24, and the ion-exchange membranes 23 and 25 are omitted, and for example, the electrode 21 of the nonworking electrode structure 2 is brought into direct contact with the biological interface coated with an electrolyte solution, whereby a drug is administered. Furthermore, the nonworking electrode structure 2 is not provided in an iontophoresis device, and for example, the working electrode structure 1 is brought into contact with the biological interface, for example the skin of a living body, while a voltage is applied to the working electrode structure 1 under the condition that a part of the living body is kept in contact with a member to serve as the ground or earth, whereby a drug is administered. In this case, the performance of suppressing the change in pH at the interface between the electrode 21 or the member to be the ground or earth, and the biological interface is not comparable to that in the above-mentioned embodiment. However, the enhancement of the administration efficiency of drug ions to a living body is similarly achieved. Such an iontophoresis device is also included in the scope of the present invention.

Furthermore, in the above embodiment, the case has been described where the working electrode structure 1, the nonworking electrode structure 2, and the power source 3 are configured separately. It is also possible that those elements are incorporated in a single casing or an entire device incorporating them is formed in a sheet shape or a patch shape, whereby the handling thereof is enhanced, and such an iontophoresis device is also included in the scope of the present invention.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ systems, circuits and concepts of the various patents, applications and publications to provide yet further embodiments of the invention.

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to other medical products, not necessarily the exemplary iontophoresis device generally described above.

What is claimed is:

1. An iontophoresis device comprising a working electrode structure, comprising:
   a first ion-exchange membrane of the working electrode structure including a first semi-permeable film of the working electrode structure with a number of pores communicating a front surface and a back surface of the first semi-permeable film of the working electrode structure and an ion-exchange resin filled in the pores of the first semi-permeable film of the working electrode structure, said first ion-exchange membrane of the working electrode structure selecting ions of a first polarity; and a drug holding part placed on a back surface side of the first ion-exchange membrane of the working electrode structure and holding a drug solution containing drug ions charged in the first polarity, the drug ions being administered via the first ion-exchange membrane of the working electrode structure, wherein a first layer of the working electrode structure having a water-soluble polymer compound chemically bonded to a material constituting the first semi-permeable film of the working electrode structure is formed on the front surface of the first semi-permeable film of the working electrode structure.

2. The iontophoresis device according to claim 1, wherein the working electrode structure further comprises:

an electrode supplied with a voltage potential of the first polarity;

an electrolyte solution holding part of the working electrode structure for holding an electrolyte solution in electrical contact with the electrode; and a second ion-exchange membrane of the working electrode structure placed on a front surface side of the electrolyte solution holding part of the working electrode structure and selecting ions of a second polarity, wherein the drug holding part is placed on a front surface side of the second ion-exchange membrane of the working electrode structure, and the first ion-exchange membrane of the working electrode structure is placed on a front surface side of the drug holding part.

3. The iontophoresis device according to claim 1, wherein the water-soluble polymer compound constituting the first layer of the working electrode structure has a straight-chain structure, and is bonded to the front surface of the first semi-permeable film of the working electrode structure in a brush shape.

4. The iontophoresis device according to claim 1, wherein the first layer of the working electrode structure is formed by irradiating, with a UV-ray, an electron beam, a γ-ray, or plasma, the first semi-permeable film of the working electrode structure immersed in an aqueous solution in which a water-soluble polymer compound is dissolved.

5. The iontophoresis device according to claim 1, wherein the water-soluble polymer compound forming the first layer of the working electrode structure is one selected from the group consisting of: polyvinyl alcohol; poly-N-isopropylacrylamide; polyacrylic acid; poly-N-methylacrylamide; polyacrylamide;

polyvinylpyrrolidone; polymethacrylic acid; polyethylene glycol; polyethyleneimine; poly-N-dimethylaminoethyl methacrylate; and polypeptide; or a mixture thereof.

6. The iontophoresis device according to claim 1, further comprising: on the front surface of the first semi-permeable film of the working electrode structure, a second layer of the working electrode structure having a water-soluble polymer compound laminated on the first layer of the water-soluble polymer compound of the working electrode structure.

7. The iontophoresis device according to claim 6, wherein the water-soluble polymer compound forming the second layer of the working electrode structure is one selected from the group consisting of: polyvinyl alcohol; poly-N-isopropylacrylamide; polyacrylic acid; poly-N-methylacrylamide; polyvinylpyrrolidone, polymethacrylic acid; polyethylene glycol; polyethyleneimine; poly-N-dimethylaminoethyl methacrylate; and polypeptide, or a mixture thereof.

8. The iontophoresis device according to claim 1, further comprising a nonworking electrode structure operating as a counterpart of the working electrode structure, the nonworking electrode structure having:

a first ion-exchange membrane of the nonworking electrode structure including a first semi-permeable film of the nonworking electrode structure with a number of pores communicating a front surface and a back surface of the first semi-permeable film of the nonworking electrode structure and an ion-exchange resin filled in the pores of the first semi-permeable film of the nonworking electrode structure, said first ion-exchange membrane of the non-working electrode structure selecting ions of a second polarity opposite to the first polarity; and an electrolyte solution holding part of the nonworking electrode structure for holding an electrolyte solution, placed on a back surface side of the first ion-exchange membrane of the nonworking electrode structure, wherein a first layer of the nonworking electrode structure having a water-soluble polymer compound chemically bonded to a material constituting the first semi-permeable film of the nonworking electrode structure is formed on the front surface of the first semi-permeable film of the nonworking electrode structure.

9. The iontophoresis device according to claim 8, wherein the working electrode structure further comprises:

an electrode supplied with a voltage potential of the first polarity;

an electrolyte solution holding part of the working electrode structure for holding an electrolyte solution in electrical contact with the electrode; and a second ion-exchange membrane of the working electrode structure placed on a front surface side of the electrolyte solution holding part of the working electrode structure and selecting ions of a second polarity, wherein the drug holding part is placed on a front surface side of the second ion-exchange membrane of the working electrode structure, and the first ion-exchange membrane of the working electrode structure is placed on the front surface side of the drug holding part.

10. The iontophoresis device according to claim 8, wherein a water-soluble polymer compound constituting one of the first layer of the working electrode structure and the first layer of the nonworking electrode structure has a straight-chain structure, and is bonded to the front surface of one of the first semi-permeable film of the working electrode structure and the first semi-permeable film of the nonworking electrode structure in a brush shape.

11. The iontophoresis device according to claim 8, wherein at least one of the first layer of the working electrode structure and the first layer of the nonworking electrode structure is formed by irradiating, with a UV-ray, an electron beam, a γ-ray, or plasma, one of the first semi-permeable film of the working electrode structure and the first semi-permeable film of the nonworking electrode structure immersed in an aqueous solution in which a water-soluble polymer compound is dissolved.

12. The iontophoresis device according to claim 8, wherein the water-soluble polymer compound forming one of the first layer of the working electrode structure and the first layer of the nonworking electrode structure is one selected from the group consisting of: polyvinyl alcohol; poly-N-isopropylacrylamide; polyacrylic acid; poly-N-methylacrylamide; polyacrylamide; polyvinylpyrrolidone; polymethacrylic acid; polyethylene glycol; polyethyleneimine; poly-N-dimethylaminoethyl methacrylate; and polypeptide; or a mixture thereof.

13. The iontophoresis device according to claim 8, further comprising: on the front surface of one of the first semi-permeable film of the working electrode structure and the first semi-permeable film of the nonworking electrode structure, a second layer of the working electrode structure or a second layer of the nonworking electrode structure having a water-soluble polymer compound laminated on one of the first layer of water soluble polymer compound of the working electrode structure and the first layer of water soluble compound of the nonworking electrode structure.

14. The iontophoresis device according to claim 13, wherein the water-soluble polymer compound forming at least one of the second layer of the working electrode structure or the second layer of the nonworking electrode structure is one selected from the group consisting of: polyvinyl alcohol; poly-N-isopropylacrylamide; polyacrylic acid; poly-N-methylacrylamide; polyvinylpyrrolidone, polymethacrylic acid; polyethylene glycol; polyethyleneimine; poly-N-dimethylaminoethyl methacrylate; and polypeptide, or a mixture thereof.

* * * * *

UNITED STATES PATENT AND TRADEMARK OFFICE
CERTIFICATE OF CORRECTION

PATENT NO. : 7,590,444 B2
APPLICATION NO. : 11/172372
DATED : September 15, 2009
INVENTOR(S) : Tanioka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 951 days.

Signed and Sealed this

Twenty-first Day of September, 2010

David J. Kappos
*Director of the United States Patent and Trademark Office*